(12) United States Patent
Aksnes et al.

(10) Patent No.: US 6,428,479 B1
(45) Date of Patent: Aug. 6, 2002

(54) ULTRASONOGRAPHY OF THE PROSTATE

(75) Inventors: Anne Kirsti Aksnes; Morten Eriksen; Else Kruger Hagen; Audun Tornes, all of Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/597,406

(22) Filed: Jun. 19, 2000

Related U.S. Application Data

(63) Continuation of application No. PCT/GB98/03807, filed on Dec. 17, 1998.
(60) Provisional application No. 60/076,805, filed on Mar. 4, 1998.

(30) Foreign Application Priority Data

Dec. 17, 1997 (GB) .............................. 9726664

(51) Int. Cl.⁷ ................................ A61B 8/00
(52) U.S. Cl. ...................................... 600/458
(58) Field of Search ................... 600/437, 439, 600/443, 447, 454–456, 459, 462–463; 601/2–3; 424/9, 52

(56) References Cited

U.S. PATENT DOCUMENTS

| 4,770,184 A | * | 9/1988 | Greene, Jr. et al. ......... 600/454 |
| 5,394,878 A | | 3/1995 | Frazin et al. |
| 5,433,204 A | | 7/1995 | Olson |
| 5,611,344 A | | 3/1997 | Bernstein et al. |
| 5,860,931 A | * | 1/1999 | Chandler ..................... 600/458 |
| 5,957,848 A | * | 9/1999 | Sutton et al. ................ 600/458 |
| 5,993,389 A | * | 11/1999 | Driscoll, Jr. et al. ........ 600/439 |
| 6,143,274 A | * | 11/2000 | Tweedle et al. ............ 424/1.65 |

FOREIGN PATENT DOCUMENTS

WO    WO 93 12720 A    7/1993

OTHER PUBLICATIONS

D. Kruse et al., "High resolution 3D flow mapping in tumors" Proceedings of the 1997 IEEE Ultrasonics Symposium, Oct. 8, 1997, XP002099481.

K. Okihara et al., "Kinetic Study of Tumor Blood Flow in Prostatic Cancer Using Power Doppler Imaging", Ultrasound in Medicine & Biology, Jan. 1998, XP002099482.

* cited by examiner

*Primary Examiner*—Francis J. Jaworski
(74) *Attorney, Agent, or Firm*—Royal N. Ronning, Jr.; Robert F. Chisholm; Stephen G. Ryan

(57) ABSTRACT

Prostate abnormalities such as cancer may be detected by ultrasonic determination of the in-flow kinetics of contrast agent-containing blood in the prostate and/or by observation of disease-related asymmetries in the spoke-like vascular pattern of the prostate.

18 Claims, No Drawings

ULTRASONOGRAPHY OF THE PROSTATE

This application is a continuation of international application number PCT/GB98/03807, filed Dec. 17, 1998 (of which the entire disclosure of the pending, prior application is hereby incorporated by reference), which itself is a continuation-in-part of provisional application No. 60/076,805, filed Mar. 4, 1998.

The present invention relates to a method of diagnosing and characterising prostate abnormalities using ultrasound contrast agent-enhanced ultrasonography, e.g. transrectal ultrasonography. In particular, the invention relates to determination of the kinetics of contrast agent in-flow and thus the state of vascularisation in the prostate as a means for such diagnosis and characterisation.

Abnormalities of the prostate gland, in particular cancer of the prostate, affect a large number of men, particularly in middle age and beyond. It is now the second leading cause of male cancer death in the USA and is becoming increasingly prevalent as longevity increases, resulting in an increased number of men of older years. Around one third of men over the age of 50 years in the USA are thought to have cancer of the prostate and approximately one tenth of these will die as a result of it.

Prostate abnormalities are primarily investigated by a combination of digital rectal examination (DRE) and evaluation of serum prostate specific antigen (PSA), possibly augmented by ultrasound or magnetic resonance imaging (MRI) techniques. Although sometimes used as an aid to diagnosis, transrectal ultrasonography (TRUS), whether or not it is augmented by the use of contrast-enhancing agents, cannot at present be relied upon to provide unequivocal diagnostic or characterising information about any prostate abnormality.

Regardless of the findings of DRE, PSA evaluation and TRUS or MRI studies, actual diagnosis of prostate abnormalities, the most common of which are cancer, prostatitis, granulomatous prostatitis, tuberculous prostatitis, prostatic intra-epithelial neoplasia, infarcts and cysts, can at present only be reliably based on samples taken from the prostate by needle biopsy. Currently, up to 10 biopsy sites are chosen randomly throughout the prostate for sampling by the clinician. This is an unsatisfactory situation since the random choice of sampling sites does not preclude the possibility of missing a cancerous lesion and thus failing to diagnose a potentially fatal disease. Furthermore, such a procedure requires detailed laboratory analysis of a large number of samples and is therefore costly and labour intensive. Needles to say, such an invasive practice is unpleasant for the patient.

Much effort has been invested in trying to improve TRUS techniques and contrast-enhancing agents so that they may, at the very least, be able to differentiate normal from abnormal tissue sufficiently well to act as a guide to the clinician in his choice of biopsy site.

Despite improvements in the enhancing ability of contrast agents and advances in imaging methods themselves, TRUS is still widely regarded as being non-specific in nature and as having made a disappointing clinical impact in this field (Downey (1997) Current Opinion in Urology 7: 93–99). also, because 25–40% of prostate tumours are isoechoic and therefore not amenable to ultrasound detection with current methods, some experts still feel that the contribution to date of ultrasonography to the diagnosis and characterisation of prostate abnormalities is minimal and disappointing (Downey supra; Bude & Rubin (1996) Radiology 200: 21–25).

Change in vascular architectured due to the induction of angiogenesis by tumour cells is known to accompany the establishment of all solid tumours, and is necessary to allow tumour development and metastasis. Studies of the changes in vascularisation which accompany tumour establishment and development quantitate the number of microvessels present in a defined area of the tissue or organ of interest, and use this to assess the degree of angiogenesis. This has been shown to correlate with disease progression in such conditions as melanoma, non-small cell lung cancer and breast cancer and can be used in predicting metastic disease.

Microvessel counts (MVCs) performed microscopically on samples taken from biopsy or prostatectomy samples have revealed a positive correlation between high MVCs and increasingly pathological stages of prostate disease (Fregene et al. (1993) Anticancer Research 13: 2377–2382). Such studies indicate that MVC determination can effectively discriminate between benign and malignant tumours and can be used to estimate confidently the likelihood of cancerous lesions in the prostate becoming metastatic.

Generally speaking, malignant tissue in the prostate, as with other body parts, has more microvessels associated with it, and hence a higher MVC, than does normal or hyperplastic tissue. Thus, determination of the state of vascularisation in defined areas of the prostate gland correlates with the state of the tissue examined. The correlation between altered vascular geometry and tissue abnormality is sufficiently close that analysis of vascularisation could be used in the diagnosis, characterisation, monitoring and prognosis of tissue abnormalities in the prostate. Unfortunately, the determination of vascular constitution or MVCs in prostate tissue may only be performed ex vivo on samples taken from a patient by biopsy.

Attempts to visualise vascular architecture in situ using TRUS have failed to generate the detail and resolution necessary to allow this technique to be reliably used for the diagnosis/monitoring of prostate abnormalities.

There is therefore a substantial need for a reliable, non-invasive method of assessing in detail the state of vascularisation in the prostate gland, in a manner which is amenable to routine clinical investigation and interpretation.

The present invention is based on the unexpected finding that abnormalities in vascular state may be assessed by ultrasonically determining certain flow parameters of contrast agent-containing blood as it traverses the prostate gland.

Thus according to one aspect, the present invention provides a method for assessing the state of vascularisation of the prostate gland by ultrasonographically determining the in-flow kinetics of an intravascularly administered ultrasound contrast agent into at least one area of the prostate.

The ultrasound image data so obtained may be used to assess one or more of blood flow, blood volume or blood perfusion in the area or areas of the prostate being imaged, so that information in respect of the whole of the prostate may be acquired.

The volume and flow rate of blood passing through the tissues of the prostate are largely determined by the number and nature of blood vessels carrying the blood. Deviations from normal vascular architecture of the prostate, even in tiny areas thereof, for example resulting from injury or tumour-induced angiogenesis, result in alterations to blood flow patterns such as the volume and flow rate and/or the number, size and compliance of the blood vessels within the organ. These changes are reflected in the flow parameters and degree or perfusion of the tissues and thus the in-flow kinetics of an ultrasound contrast agent passing through the vascular network of the prostate.

Viewed from another aspect, the present invention provides the use of an ultrasound contrast agent as an in the manufacture of an image-enhancing composition for use in the above method.

Within the contest of the present invention, the term "perfusion" may be defined as a measurement of blood volume/tissue weight/unit time. This is a difficult parameter to quantify directly, and with respect to the prostate gland probably cannot be measured in situ by any currently known technology. The degree of regional perfusion may, however, be assessed in accordance with the present invention by monitoring the temporal development of contrast effect in different regions of tissue upon arrival of the injected bolus. The arrival of contrast to tissue regions of high perfusion is expected to take place earlier than in areas of lower perfusion. However, if key variables such as the volume of conducting vessels to different tissue regions are known, the results can be directly interpreted as a quantitative measure of perfusion.

The relative degree of regional perfusion may also be assessed by power Doppler (also named "Doppler angio" or "Doppler amplitude") imaging. By proper selection of the wall motion filter characteristics, a progressive weighting of signal components from the flowing contrast agent with increasing flow velocities can be achieved. This together with the inherent linear relation between vascular volume and returned echo intensity will result in a perfusion-weighted image, since regional perfusion is well approximated by the product of vascular volume and mean flow velocity. Image data obtained in this manner may be presented to display tissue areas of varying perfusion in different colours.

As used herein the terms "determining" and "assessing" include both quantification in the sense of obtaining an absolute value for the parameter being determined or assessed and also semi-quantitative and qualitative determinations or assessments. An index, ratio, percentage or similar indication of the kinetics of in-flow of perfusion of defined areas of the prostate made by imaging an ultrasound contrast agent flowing through the vasculature therein may be obtained.

In essence, the method of invention involves administering an ultrasound contrast agent to a subject and then ultrasonically imaging the prostate of the subject by any appropriate ultrasound imaging technique, for example as known in the art. The image data so generated are used to determine one or more parameters such as volume, rate of flow, vessel diameter etc. from which the in-flow kinetics and hence the degree of perfusion may be determined.

In formation regarding the degree of tissue perfusion may be used to identify sites of abnormal vascularisation, thereby facilitating diagnosis of prostate abnormalties, evaluation of the extent or state of disease present, characterisation of any lesions identified, consideration of the best or most appropriate form of therapy and evaluation of prognosis. Alternatively, such information may be used to evaluate the efficacy of therapy or the progression or regression of disease.

In-flow kinetic data and perfusion data determined therefrom may, as described above, be used in the diagnosis, characterisation and monitoring of any abnormalities of the prostate which are accompanied by changes in vascularisation. In particular, however, conditions associated with aberrant vascularisation resulting from injury, inflammation, hyperplasia or tumour-induced angiogenesis are particularly amenable to identification in accordance with the invention. Identification and determination of the in-flow kinetics and vessel geometry of malignant and benign tumours constitutes an especially preferred embodiment of the invention.

The assessment of contrast agent in-flow kinetics provides information about temporal variations in blood flow in the prostate. Thus, by studying the time course of flow by measuring contrast increase, decrease and duration of signal generation, information from the studied area(s) may be used to distinguish normal parenchyma from abnormal tissue such as cancerous, inflamed or benign prostate hyperplastic (BPH) tissue and to distinguish between different degrees of abnormality.

Changes in vascular geometry caused by pathological conditions usually affect small vessels in particular. Deviations from the natural symmetry of the vascular pattern of the gland may also be used to identify lesions. In the practice of the present invention it is possible, if desired, actually to visualise the small vessels and their geometrical arrangements as well as to record the velocity and/or volume of blood within the vessels. Accordingly, the invention allows the mapping of vascular anatomy and architecture of the prostate to be performed concomitantly with or independently of inflow kinetic studies.

The method of the present invention has elucidated the existence of a spoke-like vascular pattern through which blood and contrast agent may be observed to flow in an inward, time-dependent, radial manner in normal prostate tissue; deviations from this symmetrical pattern may therefore represent a useful marker for evaluating and/or monitoring prostate disease. Thus, in a further aspect, the present invention provides a method for detecting prostate abnormalities in a subject which comprises administering an ultrasound contrast agent to the vascular system of said subject, ultrasonically imaging at least a part of the prostate gland of said subject and analysing the ultrasound image data so obtained for disease-related asymmetries in the spoke-like vascular pattern of the prostate.

Any appropriate ultrasound contrast agent may be used in the invention and it is clear to the person skilled in the art that different contrast agents may be more or less suitable for use with different imaging techniques, or indeed using the same imaging technique but different parameters or instrument settings. In general, any free-flowing tracer may be used.

For the assessment of perfusion of the prostate, accumulating contrast agents such as those exemplified in WO-A-9817324 may be particularly useful. Deposition of contrast agent may be related to and thus correlate with perfusion, hence facilitating the identification of the locality of cancers or other abnormalities resulting in aberrant vascular architecture and thus local variations in blood flow in the tissues.

One preferred class of ultrasound contrast agents useful in accordance with the invention comprises gas, for example, perfluorocarbon gas, microbubbles stabilised by amphiphilic material consisting essentially of phospholipid predominantly comprising molecules which individually have an overall net charge, as described in WO-A-9729783, the contents of which are incorporated herein by reference. Agents in which one or more phosphatidylserines constitute at least 70% of the phospholipid content and in which the gas content comprises sulphur hexafluoride or a $C_{1-6}$ fluorinated (e.g. perfluorinated) hydrocarbon such as perfluoropropane, perfluorobutane or perfluoropentane are particularly preferred.

Any appropriate ultrasound imaging technique may be used in the method of the invention, for example fundamental B-mode imaging; harmonic B-mode imaging including reception of sub-harmonics, the second and higher harmonics and sums and differences of specific harmonics; and Doppler techniques such as tissue Doppler imaging, optionally including selective reception of fundamental, harmonic or sub-harmonic echo frequencies; colour Doppler imaging, optionally including selective reception of fundamental, harmonic or sub-harmonic echo frequencies; power Doppler imaging, optionally including selective reception of fundamental, harmonic or sub-harmonic echo frequencies; power or colour Doppler imaging utilising loss of correlation or apparent Doppler shifts caused by changes in the acoustic properties of contrast agent microbubbles such as may be caused by spontaneous or ultrasound-induced destruction, fragmentation, growth or coalescence; pulse inversion imaging, optionally including selective reception of fundamental, harmonic or sub-harmonic echo frequencies, and also including techniques wherein the number of pulses emitted in each direction exceeds two; pulse inversion imaging utilising loss of correlation caused by changes in the acoustic properties of contrast agent microbubbles such as may be caused by spontaneous or ultrasound-induced destruction, fragmentation, growth or coalescence; Pulse pre-distortion imaging, e.g. as described in 1997 IEEE Ultrasonic Symposium, pp 1567–1570; ultrasound imaging techniques based on comparison of echoes obtained with different emission output amplitudes or waveform shapes in order to detect non-linear effects caused by the presence of gas bubbles; ultrasound imaging techniques where images are taken at different acoustic output levels such as one with high power and up to ten (e.g. two or three) are taken at low power; ultrasound imaging techniques based on comparison of echoes obtained with any one the above mentioned techniques, in order to study the wash-in of contrast agent (e.g. time-intensity profile) after the agent has been destroyed or modified by one of several high energy ultrasound pulses, for example by transmitting a series of high energy pulses at high frame-rate followed by a series of low amplitude pulses at low frame-rate (fixed rate or triggered by the ECG signal); ultrasound imaging techniques based on comparison of echoes obtained with any one the above mentioned techniques, in order to study spatial and temporal speckle variations after injection of a contrast agent as described in WO-A-9712551; ultrasound imaging techniques based on detecting local aberrations in vasculated tissue perfusion and/or compliance by generating waveforms representative of arterial pulsatility and analysing said waveforms for variations characteristic of local aberrations in perfusion and/or compliance, as described in our International Application of even date based on UK Patent Application No. 9726773.6; and ultrasound imaging techniques where the images are gated to the cardiac cycle, e.g. ECG, or gated to other physical movements such as breathing, for example as described in U.S. Pat. No. 5,735, 281.

Of the above mentioned techniques, power Doppler is a preferred one. Other preferred techniques are pulse inversion and second harmonic B-mode imaging particularly combined with analysis of temporal contrast-induced speckle variations, enabling assessment of the local vessel architecture and degree of vascularity with high resolution and sensitivity. These technqiues may be further combined with subtraction of the tissue background signal.

Combining any of the above mentioned techniques with three dimensional acquisition and reconstruction the ultrasound image is possible, allowing assessment of the three dimensional vessel architecture and vascular state to be performed. Doppler based methods can be used for this purpose, but pulse inversion and second harmonic B-mode imaging are preferred as they provide excellent spatial resolution and are independent of direction and rate of flow, and hence may provide information on vascular geometry and vascular state with excellent resolution, as well as information regarding the microcirculation. A further improvement may be obtained by combining with speckle variation analysis and employing tissue background substraction, the use of power Doppler being preferred in such embodiments.

A single imaging technique may be used in practising the method of the invention or a number or combination of different imaging techniques may be used in a single investigative session to determine the in-flow kinetics. Depending on the particular site within the prostate being examined, e.g. whether peripheral, periurethral or parenchymal regions are examined, different contrast agents, imaging techniques or combinations thereof may provide better resolution or definition or reduced noise or motion-induced artefacts. Such flexibility is an advantage of the method of the invention and information generated by more than one ultrasound contrast agent and/or more than one imaging technique may be used in performing the method of the invention.

Techniques as disclosed in the aforementioned International Application of even date based on UK Patent Application No. 9726773.6 include the use of power Doppler imaging, i.e. Doppler imaging in which signal intensities in respect of velocities above a certain level are measured, in conjunction with intravascularly administered contrast agent to identify local aberrations in vasculation tissue perfusion and/or compliance. As well as giving a general increase in signal intensity which enables visualisation of blood flow within very small vessels, the presence of contrast agent improves the signal-to-noise ratio compared to imaging without contrast agent, thereby permitting use of a shorter temporal image averaging time constant than is normally employed in power Doppler imaging. This in turn allows the visualisation of waveforms representing arterial pulsatility in perfused tissue, for example as cardiac-synchronous pulsatile flashing patterns. Analysis of such pulsatile patterns to detect the temporal and spatial pattern of variation in the Doppler signal permits significantly more precise detection and imaging of local aberrations in tissue perfusion and/or compliance than do the hitherto used methods based on Doppler velocity waveform indices. Such embodiments facilitate tumour detection since the lack of vasuclar tissue differentiation in malignant tumour vessels may cause resistance and compliance conditions different from normal tissue.

Imaging techniques such as B-mode imaging, especially harmonic techniques such as second harmonic B-mode imaging, may, for example, be used to record arterial pulsatility waveforms generated as a result of volume pulsations induced within the vascular system of the prostate by the cardiac cycle.

Any appropriate imaging equipment operating in intensity mode may be employed, for example comprising a phased-array sector or linear array ultrasound scanner. In Doppler investigations that tissue movement artefact filter is advantageously set to a relatively high value, and is preferably selected to have characteristics which result in smoothly decreasing signal sensitivity as velocities approach zero; filters having a linear power versus frequency curve are particularly preferred. Such high-pass filtering modulates the intensity of the displayed signal in a linear manner and may generate a pulsatile pattern as arterial blood velocities vary from being above and below the threshold. It is generally preferred that the intensity signal should be processed linearly with no logarithmic compression; such processing may be effected without regard to background tissue echo properties.

In order to enhance the sensitivity of phase shift detection, signal detection is preferably made with respect to a frequency and phase reference, for example derived from an electrocardiogram (ECG) or similar cardiac-synchronous signal. Other natural rhythms such as the respiratory cycle may similarly be used; venous flow velocities are modulated by respiration, as is the sympathetic innervation of peripheral resistance vessels. Alternatively or additionally, externally applied reference pulses, e.g. with frequencies of up to 100 Hz, may be used; thus, for example, a mechanical vibrator may be positioned above a major artery so as to transmit pressure pulsations into the bloodstream.

Signal processing may be effected by calculating the phase and amplitude of the intensity signal pulsation at the reference frequency or a whole number multiple thereof for each relevant pixel in the image, for example using a Fourier transform; if desired, the image may first be decimated by two dimensional low-pass filtering and re-sampling. If a series of Doppler intensity images $(I_1, I_2 \ldots I_N)$ within a cardiac reference cycle are obtained at times $t_1, t_2 \ldots t_N$ and two successive ECG r-wave detection events defining this cycle occur at $T_1$ and $T_2$, then the complex Fourier sum at a given $p^{th}$ harmonic of the heart rate for a given pixel (x,y) can be calculated as $$P_{p,x,y} = \sum_n I_{n,x,y} \exp\left[\frac{j2\pi p(t_n - T_1)}{T_2 - T_1}\right]$$

This calculation may be repeated for a number of successive cardiac cycles, and the resulting Fourier coefficients may be averaged to improve the signal-to-noise ratio. Alternatively, such averaging may be effected for real-time applications by time constant low-pass filtering.

The complex Fourier coefficient may, for example, be used to construct a coloured imaging which may if desired be overlaid on a grey scale tissue image. Thus, for example, complex values based on Fourier coefficients for the fundamental heart rate frequency (p=1) may be encoded with the absolute value as brightness and the phase as colour (e.g. using a continuous circular rainbow scale). Areas of detectable perfusion will then be more or less bright, whilst regions of compromised circulation will be identified by colour variations indicative of phase distortion. Information contained in higher harmonics of the heart rate frequency (p>1) may additionally or alternatively be used to increase the sensitivity of phase shift detection.

Alternatively, several simultaneous variables may be calculated and used in multivariate statistical tissue characterisation. Representative variables which may be used in this way are the phase and amplitude of the signal at the heart rate or a harmonic thereof, the temporal mean value of the signal intensity and the peak signal intensity during a cardiac cycle.

Techniques such as ECG-gated coherent averaging may be used to build up and accurate map or regional pulsatility for a whole image; if desired, empirical pulsatility indices may be calculated and displayed, for example as a colour overlay image. A reasonable estimate of the coherent averaged cycle may be obtained by reverse Fourier transformation of discrete coefficients for a limited set of values of p or by performing coherent averaging in time domain, compensating for the variable duration of cardiac cycles by time axis interpolation.

A further improvement may be obtained by combining any of the above mentioned techniques with three dimensional acquisition and reconstruction of the ultrasound image, allowing assessment of the three dimensional vessel architecture and vascular state to be performed. Doppler based methods may be used for this purpose, but pulse inversion imaging and harmonic imaging techniques such as second harmonic B-mode imaging may be preferred as they provide excellent spatial resolution and are independent on direction and rate of flow and hence these methods may provide information on vascular geometry and vascular state with excellent resolution containing information of the microcirculation. A further improvement may be obtained in combination with speckle variation analysis and/or tissue background subtraction.

In the method of the invention in general, the means for transmitting and receiving the ultrasound signals may be any appropriate means known to one skilled in the art but is preferably a transrectal transducer. Such transducers may be brought into close proximity with the target area, with the consequential advantage that signal attenuation by intervening tissue etc. is minimised. Since attenuation increases with frequency this permits use of relatively high frequency ultrasound irradiation so as to obtain images with enhanced resolution.

The frequency at which the ultrasound signals may be transmitted and/or received may, for example, be in the range 0.1–1.18 MHz, e.g. 4–11 MHz and more preferably between 6 and 9 MHz. Depending on the nature of the imaging technique, the frequency of the received signal may be the same as that of the transmitted signal, for example as in fundamental B-mode imaging, or it may be a harmonic thereof, for example as in second harmonic imaging, where if the transmitted signal has as frequency of 4 MHz the signal received will have a frequency of 8 MHz.

An important advantage of the present invention is that ultrasound image data from essentially any area of the prostate may be analysed and the in-flow kinetics and degree of perfusion from the assessed areas determination. A hitherto unobtainable thoroughness and clarity may be achieved and essentially every area of the entire gland may be analysed for areas of abnormal vascularisation. The benefit of this method relative to the random needle biopsy sampling is clearly substantial, particularly in terms of clinical confidence, accuracy and reliability.

The ability to reliably assess vascularisation, for example using TRUS technology signifies a great step forward in this field by allowing physicians to visualise essentially any site on or in the prostate, in a non-invasive manner and the ability to generate high quality images allows detailed assessment of the state or vascularisation in an indirect manner. Thus, all areas and not just randomly selected areas of the prostate may be analysed in a single screening procedure and a more thorough examination of the whole prostate is performed. Clearly the method of the invention is much more satisfactory form a clinical point of view and is also much more acceptable to the patient. Even when biopsy sampling still proves necessary unequivocally to identify the nature of a lesion, the method of the present invention allows the clinician specifically to identify the sites in need of biopsy and dispenses the need for random "hit and miss" sampling.

The following non-limitative examples serve to illustrate the invention.

Preparation 1 a) Perfluorobutane gas dispersion

Hydrogenated phosphatidylserine (100 mg) in 20 ml of an aqueous solution of propylene glycol (0.3 g) and glycerol (1.0 g) was stirred at 80° C. for 20 minutes and the resulting liquid mixture was allowed to cool to room temperature. The headspace above the liquid was flushed with perfluorobutane gas and upon sonication yielded a milky white microbubble dispersion.

b) Dispersion of lyophilised perfluorobutane gas dispersion

A sample of the milky white dispersion prepared as in (a) above was washed 5–10 times by flotation and removal of the infranatant. The sample was redispersed in water for injection. The washed gas dispersion was mixed with an equal volume of 10% sucrose solution. Volume median diameter was determined at room temperature to be in the range 3 to 4 micrometers by a Coulter Counter instrument fitted with a 50 $\mu$m aperture and having a measuring range 1–30 $\mu$m, Isoton II was used as electrolyte.

1 ml portions of the washed gas dispersion in 5% sucrose were transferred to 2 ml vials and lyophilised. Redispersion for injection was done in water to a microbubble concentration of 5–15 $\mu$l/ml.

EXAMPLE 1

Imaging of Normal Prostate after injection of ultrasound contrast agent

An HDI 3000 ultrasound scanner with a C9-5 ICT transrectal probe was used to examine a 24 kg male mongrel dog sedated by intramuscular administration of a mixture of 0.04 mg/kg atropine sulfate. 0.75 mg/kg acepromazine and 23 mg/kg ketamine hydrochloride. Sedation was maintained with intravenous injections of 8 mg/kg pentobarbital.

An 18 gauge angiocatheter was placed in a forelimb vein, a dose of 0.0125 $\mu$l microbubbles/kg of the contrast agent of Preparation 1 were injected, and power Doppler images being recorded before and after injection. The instrument settings were adjusted to obtain optimal contrast images.

13 seconds after injection of contrast agent very few vessels could be seen and there was no significant contrast enhancement. At 15 seconds after injection contrast began to appear in the peripheral regions on both sides of the prostate, indicating that the blood supply to the prostate starts in the peripheral region. At 16 seconds after injection contrast had advanced from the peripheral regions towards the centre of the prostate and a spoke-like vascularity pattern was evident; this became better visualised over the next few seconds.

EXAMPLE 2

Prostate ablation

An HDI 3000 ultrasound scanner with a C9-5 ICT transrectal probe was used to examine a 25 kg male mongrel dog sedated by intramuscular administration of a mixture of 0.04 mg/kg atropine sulfate, 0.75 mg/kg acepromazine, and 23 mg/kg ketamine hydrochloride. Sedation was maintained with intravenous injections of 8 mg/kg pentobarbital.

An 18 gauge angiocatheter was placed in a forelimb vein, a dose of 0.006 $\mu$l microbubbles/kg of the contrast agent of Preparation 1 were injected, and fundamental B-mode and power Doppler images were recorded. The instrument settings were adjusted to obtain optimal contrast images. The spoke-like vascular pattern described in Example 1 was clearly recognisable approximately 3 minutes after injection of contrast agent.

A laser tissue ablation needle was placed in a targeted area of the prostate using a transurethral approach, and ablation was performed with a 10 watt laser irradiation for 3 minutes. Neither the location nor the size of the resulting ablation could be visualised using B-mode imaging or power Doppler imaging in the absence of contrast agent. However, approximately 2 minutes after injection of contrast agent, it was possible to detect a normal spoke-like vascularity pattern on the left side of the prostate and a disturbance of normal vascularity on the right side, this representing the ablation.

EXAMPLE 3

2nd Harmonic B-mode imaging

An HDI 3000 ultrasound scanner with a L10-5 ICT linear array transabdominal probe was used to examine a 24 kg male mongrel dog sedated by intramuscular administration of a mixture of 0.04 mg/kg atropine sulfate, 0.75 mg/kg acepromazine, and 23 mg/kg ketamine hydrochloride. Sedation was maintained with intravenous injections of 8 mg/kg pentobarbital.

An 18 gauge angiocatheter was placed in a forelimb vein, a dose of 0.1 $\mu$l microbubbles/kg of contrast agent from Preparation 1 was injected and continuous second harmonic B-mode imaging was performed. The instrument settings were adjusted to obtain optimal contrast images.

Contrast enhancement caused by the presence of contrast agent was seen throughout the prostate, as expected for a normal gland where all areas are perfused. The relatively homogenous appearance of the image indicated that contrast agent present in small vessels and capillaries was detected.

EXAMPLE 4

Imaging of the normal prostate in human volunteers

After pre-study screening, including physical examination and medical history analysis, 5 healthy male volunteers aged 18 to 25 years old were included in a phase II clinical study to evaluate the vascular pattern in the prostate.

Firstly, baseline examinations of the prostate were performed in both transverse and longitudinal projections. Three different imaging modalities were used: fundamental B-mode, followed sequentially either by colour Doppler and then power Doppler, or by power Doppler and then colour Doppler. The same procedure was repeated after injection of the contrast agent (Preparation 1).

For fundamental B-mode imaging, a dose of 0.3 $\mu$l microbubbles/kg was given. For the more sensitive Doppler techniques lower doses (0.03 $\mu$l microbubbles/kg) were given. Multiple injections were given, one before each view (transverse and longitudinal projection) using the three different imaging modalities.

The contrast agent was injected at a rate of approximately 1 ml per second by connecting the syringe directly to a venflon (18G cannula) port.

Acuson Sequoia No. 512 ultrasound equipment with an endocavital transducer was operated at 7 MHz, with images being recorded before and after contrast agent injection. The instrument settings were adjusted to obtain optimal contrast images. Vascular patterns of the prostate were subjectively evaluated using an ordinal 4-point scale (poor, fair, good, excellent).

Normal vascularity was further described by the following observations:

Filling from the periphery to the center (yes/no)
Radial Pattern (yes/no)
Symmetry (yes/no)
Evaluation of the images obtained revealed results similar to those of Example 1. Visualisation of the vascular pattern of the normal prostate was distinctly better after the contrast agent appeared in the prostate. The contrast appeared first in the peripheral region, and subsequently drained toward the center of the prostate. A spoke-like vascular pattern of the prostate was observed. Colour Doppler and power Doppler images were distinctly better and revealed more detail than fundamental B-mode imaging.

EXAMPLE 5

Imaging of the prostate in subjects suspected of having prostate cancer

Male subjects suspected of having prostate cancer and scheduled for transrectal ultrasound-guided core biopsy of the prostate at an outpatients department were included in the study. Positive indicators of prostate cancer were elevated prostate specific antigen, positive digital rectal examination and fine needle aspiration biopsy, either alone or in combination.

Firstly, baseline examinations of the prostate were performed, in both the transverse and longitudinal projections. Three different imaging modalities are used: fundamental B-mode, followed sequentially either by colour and then power Doppler, or by power Doppler and then colour Doppler. After the baseline examination, the same procedure was repeated after injection of the contrast agent (Preparation 1).

For fundamental B-mode imaging, a dose of 0.3 $\mu$l microbubbles/kg was given. For the more sensitive Doppler techniques lower doses (0.03 $\mu$l microbubbles/kg) were given.

The injection of the contrast agent was performed at a rate of approximately 1 ml per second by connecting the syringe directly to a venflon (18G cannula) port.

Acuson Sequoia No. 512 ultrasound equipment with an endocavital transducer is operated at 7 MHz. The instrument settings were adjusted to obtain optimal contrast images.

In a representative power Doppler imaging procedure, contrast enhancement was observed to begin in the peripheral zone on the right side of the prostate about 20 seconds after injection of contrast agent. 28 seconds after injection of contrast agent, this area showed a highly significant contrast enhancement compared to the corresponding area on the left side of the prostate. In addition, the vascular architecture within the area on the right side of the prostate indicated that this area contained pathological tissue. 40 seconds after injection of contrast, contrast enhancement was more equally distributed throughout the prostate and only the different vascular architecture in the peripheral zone on the right side of the prostate indicated pathological tissue.

Confirmation of prostate cancer by biopsy

Core biopsies taken from the area where contrast first appeared showed a marked enhancement and had a different vascular architecture compared to the left side of the prostate. The biopsies verified that the subject had prostate cancer, located in an area within the peripheral zone at the right side of the prostate.

Comparison between imaging modalities

Imaging of the same subject as described above using power Doppler, was also done using fundamental B-mode and colour Doppler imaging. Colour and power Doppler images gave essentially the same information, and these methods were distinctly better, revealing more detailed information than fundamental B-mode imaging.

Thus, in-flow kinetics and vascular architecture of different areas of the human prostate were possible to evaluate after injection of contrast agent. This information can be used to distinguish between the normal and pathological tissue.

EXAMPLE 6

Imaging of the prostate in a human subject with prostate cancer

A human subject with known prostate carcinoma is imaged by harmonic power Doppler ultrasound. The instrument is adjusted for a high frame rate with no image persistance. The subject's ECG is recorded simultanteously.

A bolus (0.03 $\mu$l microbubbles/kg) of the contrast agent described in Preparation 1 is then injected and a 10 second sequence of ultrasound images is recorded by digital means in the steady state blood pool recirculation phase of the contrast agent. The images are analysed by extracting the exact frequency and phase of the heart rate from the ECG r-waves and calculating the discrete complex Fourier coefficient at this frequency for the temporal variations in brightness for each pixel in the image. A new image is then calculated, where local brightness is derived from the magnitude of the Fourier coefficient and colour is derived from the phase. The brightness and the colour of the lesions will differ from the surrounding normal prostate tissue due to differences in microvascular resistance and compliance between the tissues.

What is claimed is:

1. A method for diagnosing prostate disease in a subject which comprises:
   intravascularly administering an ultrasound contrast agent to said subject, ultrasonically determining flow and/or volume kinetic data in respect of contrast agent-containing blood flowing into and traversing at least a part of the prostate gland of said subject, and analysing said kinetic data to identifying disease-induced changes in vascularity within the prostate gland.

2. A method as claimed in claim 1 wherein the ultrasound contrast agent is administered as a bolus and said kinetic data is determined by monitoring temporal development of contrast effect caused by arrival of said bolus in different regions of prostate tissue.

3. A method as claimed in claim 1 wherein ultrasound image data in respect of inward flow of contrast agent-enhanced blood within the spoke like vascular pattern of the prostate are generated.

4. A method as claimed in claim 1 wherein perfusion-weighted ultrasound image data are generated using power Doppler imaging.

5. A method as claimed in claim 1 wherein ultrasound image data are processed to generate waveforms representative of arterial pulsatility and said waveforms are analysed for variations characteristic of local aberrations in tissue perfusion and/or compliance within the prostate.

6. A method as claimed in claim 5 wherein the ultrasound image data are generated by power Doppler imaging.

7. A method as claimed in claim 6 wherein the ultrasound image data are processed by high-pass filtering at a threshold such that a pulsatile pattern is generated as arterial blood velocity varies above and below said threshold.

8. A method as claimed in claim 5 wherein the ultrasound image data are processed with respect to a frequency and phase reference.

9. A method as claimed in claim 8 wherein said frequency and phase reference is a cardiac-synchronous signal.

10. A method as claimed in claim 8 wherein the ultrasound image data are processed to generate phase information, and phase shift detection is employed to identify potential local aberrations in tissue perfusion and/or compliance within the prostate.

11. A method as claimed in claim 8 wherein the ultrasound image data are generated by power Doppler imaging, harmonic imaging or pulse inversion imaging.

12. A method as claimed in claim 1 which is combined with three dimensional acquisition and reconstruction of ultrasound image data.

13. A method as claimed in claim 1 wherein the ultrasound contrast agent comprises gas microbubbles stabilised by amphiphilic material consisting essentially of phospholipid predominantly comprising molecules which individually have an overall net charge.

14. A method as claimed in claim 13 wherein the amphiphilic material comprises one or more phosphatidylserines constituting at least 70% of the phospholipid content and in which the gas content of the microbubbles comprises sulphur hexafluoride or a $C_{1-6}$ fluorinated hydrocarbon.

15. A method as claimed in claim 14 wherein the gas content of the microbubbles comprises perfluoropropane, perfluorobutane and/or perfluoropentane.

16. A method as claimed in claim 1 wherein the ultrasound image data are generated using a transrectal transducer.

17. A method as claimed in claim 1 wherein said identification of disease-induced changes in vascularity within the prostate is used in diagnosis of prostate abnormalities, identification of sites in need of biopsy, evaluation of extent or state of disease, characterisation of identified lesions, consideration of best or most appropriate form of therapy, evaluation of prognosis, evaluation of efficacy of therapy, evaluation of progression or regression of disease, or identification of conditions associated with aberrant vascularisation resulting from inflammation, hyperplasia or tumour-induced angiogenesis.

18. A method for diagnosing prostate disease in a subject which comprises administering an ultrasound contrast agent to the vascular system of said subject, ultrasonically imaging at least a part of the prostate gland of said subject and analysing the ultrasound image data so obtained for disease-related asymmetries in the spoke-like vascular pattern of the prostate.

* * * * *